(12) United States Patent
Furukawa et al.

(10) Patent No.: US 6,821,766 B1
(45) Date of Patent: Nov. 23, 2004

(54) THERMOSTABLE CREATINE AMIDINOHYDROLASE AND PROCESS FOR PRODUCING THE SAME

(75) Inventors: Keisuke Furukawa, Chiba (JP); Yasuji Koyama, Chiba (JP); Masaru Suzuki, Chiba (JP)

(73) Assignee: Kikkoman Corporation, Chiba (JP)

( * ) Notice: Subject to any disclaimer, the term of this patent is extended or adjusted under 35 U.S.C. 154(b) by 0 days.

(21) Appl. No.: 09/869,280

(22) PCT Filed: Dec. 28, 1999

(86) PCT No.: PCT/JP99/07424

§ 371 (c)(1),
(2), (4) Date: Jun. 27, 2001

(87) PCT Pub. No.: WO00/40708

PCT Pub. Date: Jul. 13, 2000

(30) Foreign Application Priority Data

Jan. 1, 1999 (JP) .............................. 11/33359

(51) Int. Cl.[7] .............................. C12N 9/14; C12N 9/78
(52) U.S. Cl. ...................................... 435/195; 435/227
(58) Field of Search ................................ 435/227, 195

(56) References Cited

U.S. PATENT DOCUMENTS

| | | | |
|---|---|---|---|
| 3,806,416 A | * | 4/1974 | Mollering et al. |
| 3,907,644 A | * | 9/1975 | Mollering et al. |
| 3,912,588 A | | 10/1975 | Möllering et al. |
| 4,039,384 A | | 8/1977 | Suzuki et al. |
| 4,990,453 A | * | 2/1991 | Schumacher et al. |
| 5,451,520 A | * | 9/1995 | Furukawa et al. |
| 5,932,466 A | | 8/1999 | Furukawa et al. .......... 435/227 |
| 6,080,553 A | * | 6/2000 | Sogabe et al. |

FOREIGN PATENT DOCUMENTS

| | | |
|---|---|---|
| DE | 19536506 A1 | 4/1996 |
| EP | 0 291 321 A2 | 11/1988 |
| EP | 0 790 303 A1 | 8/1997 |
| EP | 9-215494 | 8/1997 |
| JP | 62091182 * | 4/1987 |
| JP | 8-89255 | 4/1996 |
| JP | 10174585 * | 6/1998 |
| WO | WO 00/31245 | 6/2000 |

OTHER PUBLICATIONS

Supplementary European Search Report, for corresponding European Patent Application No. 99961487.8, dated Oct. 7, 2002.
U.S. patent application Ser. No. 09/856,645, Furukawa et al., filed May 24, 2001.
International Search Rpeort for PCT/JP99/06583, dated Feb. 21, 2000.

* cited by examiner

*Primary Examiner*—Michael Meller
(74) *Attorney, Agent, or Firm*—Finnegan, Henderson, Farabow, Garrett, & Dunner, L.L.P.

(57) ABSTRACT

The present invention relates to a thermostable creatine amidinohydrolase having the following physicochemical properties: (a) hydrolyzing 1 mol of creatine to give 1 mol of sarcosine and 1 mol of urea; (b) having a substrate specificity to creatine; (c) having an optimum pH of 7.0 to 8.0; (d) having a stable pH range of 4.0 to 11.0; (e) having the optimum temperature of around 45° C.; (f) being thermostable at 53° C.; (g) having a molecular weight of 92,000 Da (as determined by gel filtration), and to a process for producing the thermostable creatine aimdinohydrolase.

2 Claims, 4 Drawing Sheets

SEQUENCE LISTING

<160> NUMBER OF SEQ ID NOS: 1

<210> SEQ ID NO 1
<211> LENGTH: 404
<212> TYPE: PRT
<213> ORGANISM: Alcaligenes sp.

<400> SEQUENCE: 1

```
Met Thr Asp Asp Met Leu His Val Met Lys Trp His Asn Gly Glu Lys
 1               5                  10                  15

Asp Tyr Ser Pro Phe Ser Asp Ala Glu Met Thr Arg Arg Gln Asn Asp
            20                  25                  30

Val Arg Gly Trp Met Ala Lys Asn Asn Val Asp Ala Ala Leu Phe Thr
        35                  40                  45

Ser Tyr His Cys Ile Asn Tyr Tyr Ser Gly Trp Leu Tyr Cys Tyr Phe
    50                  55                  60

Gly Arg Lys Tyr Gly Met Val Ile Asp His Asn Asn Ala Thr Pro Ile
65                  70                  75                  80

Ser Ala Gly Ile Asp Gly Gly Gln Pro Trp Arg Arg Ser Phe Gly Asp
                85                  90                  95

Asn Ile Thr Tyr Thr Asp Trp Arg Arg Asp Asn Phe Tyr Arg Ala Val
            100                 105                 110

Ala Gln Leu Thr Thr Gly Ala Lys Arg Ile Gly Ile Glu Phe Asp His
        115                 120                 125

Val Asn Leu Asp Phe Arg Arg Gln Leu Glu Glu Asn Leu Pro Gly Val
    130                 135                 140

Glu Phe Val Asp Ile Ser Gln Pro Ser Met Trp Met Arg Thr Ile Lys
145                 150                 155                 160

Ser Leu Glu Glu Gln Lys Leu Ile Arg Glu Gly Ala Arg Val Cys Asp
                165                 170                 175
```

-continued

```
Val Gly Gly Ala Ala Cys Ala Ala Ala Ile Lys Ala Gly Val Pro Glu
            180             185              190

His Asp Met Ala Ile Ala Thr Thr Asn Ala Met Ile Arg Glu Ile Ala
        195             200              205

Lys Ser Phe Pro Phe Val Glu Leu Met Asp Thr Trp Thr Trp Phe Gln
    210             215              220

Ser Gly Ile Asn Thr Asp Gly Ala His Asn Pro Val Thr Asn Arg Ile
225             230              235              240

Val Gln Ser Gly Asp Ile Leu Ser Leu Asn Thr Phe Pro Met Ile Phe
            245             250              255

Gly Tyr Tyr Asn Pro Leu Glu Arg Thr Leu Phe Cys Asp His Val Asp
            260             265              270

Asp Ala Ser Leu Asp Ile Trp Glu Lys Asn Val Ala Val His Arg Arg
            275             280              285

Gly Leu Glu Leu Ile Lys Pro Gly Ala Arg Cys Lys Asp Ile Ala Ile
            290             295              300

Glu Leu Asn Glu Met Tyr Arg Glu Trp Asp Leu Leu Lys Tyr Arg Ser
305             310              315              320

Phe Gly Tyr Gly His Ser Phe Gly Val Leu Cys His Tyr Tyr Gly Arg
            325             330              335

Glu Ala Gly Val Glu Leu Arg Glu Asp Ile Asp Thr Glu Leu Lys Pro
            340             345              350

Gly Met Val Val Ser Met Glu Pro Met Val Met Leu Pro Glu Gly Met
            355             360              365

Pro Gly Ala Gly Gly Tyr Pro Glu His Asp Ile Leu Ile Val Gly Glu
    370             375              380

Asp Gly Ala Glu Asn Ile Thr Gly Phe Pro Phe Gly Pro Glu His Asn
385             390              395              400

Ile Ile Arg Asn
```

THERMOSTABLE CREATINE AMIDINOHYDROLASE AND PROCESS FOR PRODUCING THE SAME

FIELD OF THE INVENTION

The present invention relates to a thermostable creatine amidinohydrolase and a process for producing the same.

BACKGROUND OF THE INVENTION

Creatine amidinohydrolase is an enzyme catalyzing hydrolysis of creatine to give sarcosine and urea, which can be used to determine an amount of creatine in human serum or urine, being usable as a diagnostic agent for various diseases such as kidney diseases and the like.

For the reason that a creatine amidinohydrolase from Alcaligenes having Km value of approximately 13 mM and thermostability of around 45° C. shows a lower Km value, and moreover, taking into consideration the distribution and the sales of the agent in liquid form, a creatine amidinohydrolase having stability at an increased temperature has been sought. Furthermore, conventionally, attempts to improve the thermostability of creatine amidinohydrolase by genetic modification frequently ended with the results showing the same Km value as an original strain or even a decreased value, and there have been no cases where the thermostability and the Km value thereof were improved.

The object of the present invention is to provide a thermostable creatine amidinohydrolase and a process for producing the same.

SUMMARY OF THE INVENTION

The present inventors have further studied to solve the above problem, and found that a thermostable creatine amidinohydrolase was obtainable by modifying a gene of an Alcaligenes creatine amidinolhydrolase (JP-A-8-89255 (1996)), thus completing the present invention.

In one aspect, the present invention provides an isolated thermostable creatine amidinohydrolase having the following physicochemical properties:

(a) hydrolyzing 1 mol of creatine to give 1 mol of sarcosine and 1 mol of urea;

(b) having a substrate specificity to creatine;

(c) having an optimum pH range of 7.0 to 8.0;

(d) having a stable pH range of 4.0 to 11.0;

(e) having the optimum temperature of around 45° C.;

(f) being thermostable at 53° C.; and (g) having a molecular weight of 92,000 Da (as determined by gel filtration).

In an embodiment, the thermostable creatine amidinohydrolase of the present invention is derived from an Alcaligenes bacterium.

In another embodiment, the thermostable creatine amidinohydrolase of the invention is generated by introducing a mutation(s) into a gene of the Alcaligenes creatine amidinohydrolase and allowing expression of the obtained genetic mutant.

In another embodiment, the thermostable creatine amidinohydrolase of the invention has an amino acid sequence comprising a mutation(s) relative to the amino acid sequence of SEQ ID NO:1. The term "mutation" as used herein means at least one amino acid substitution, addition, insertion, or deletion.

Furthermore, in another embodiment, the thermostable creatin amidinohydrolase of the invention can be produced by an E.coli JM109 strain (pUCE100 B-40) (Accession Number: FERM BP-6867) or a strain derived therefrom.

In another aspect, the invention provides a process for producing the thermostable creatine amidinohydrolase which comprises incubating a microorganism capable of producing the above amidinohydrolase, and recovering said amidinohydrolase from the culture.

In another embodiment of the invention, said microorganism is an E.coli JM109 strain (pUCE100 B-40) (Accession Number: FERM BP-6867) or a strain derived therfrom.

The term "strain derived therefrom" as used herein means a mutant which can be obtained by natural or artificial mutagenesis of E.coli JM109 (pUCE100 B-40), the mutant being a strain capable of producing the thermostable creatine amidinohydrolase with physicochemical properties equivalent to those mentioned above.

DETAILED DESCRIPTION OF THE INVENTION

Figure 1:
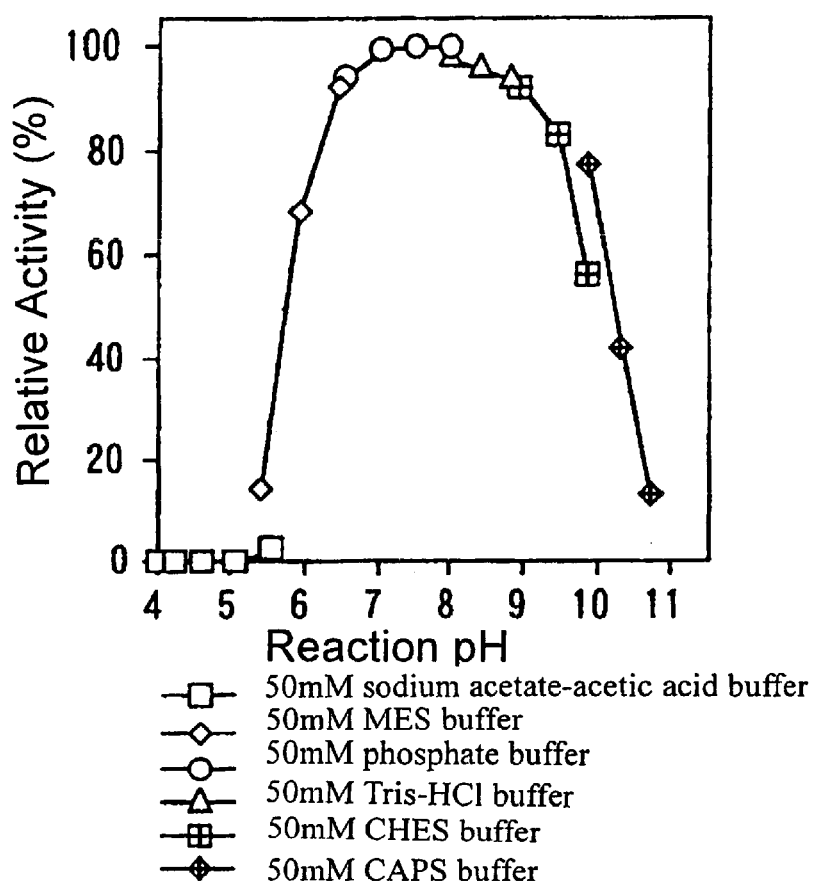
FIG. 1 shows the optimum pH of the enzyme of the invention.

The present invention will be described in detail below.

The creatine amidinohydrolase can be obtained, for example, as follows.

In one method, a mutant can be produced artificially by exposing an Alcaligenes bacterium to radiation such as a UV light or by treating said bacterium with chemical mutagens (such as nitrous acid, hydroxylamine, etc.) to obtain mutants and selecting a mutant having the thermostable creatine amidinohydrolase activity of the present invention from the obtained mutants according to a method for determining enzyme properties such as the method mentioned below. The mutant with the activity of interest is incubated in a suitable medium to collect the thermostable creatine amidinohydrolase produced thereby.

In an alternative method, DNA encoding the thermostable creatine amidinohydrolase can be obtained from an Alcaligenes bacterium or a mutant strain thereof according to usual methods, or DNA encoding the creatine amidinohydrolase can be mutated into DNA encoding the thermostable creatine amidinohydrolase with mutagenesis treatment.

For example, DNA of interest can be obtained as follows. Genomic DNA or mRNA is taken from the above bacterium, and in the case of genomic DNA, said DNA is cut into an appropriate length to incorporate it into a suitable vector to create a genomic DNA library, while in the case of mRNA, cDNA library is created with reverse transcriptase, followed by performance of an immunological reaction with an anti-creatine amidinohydrolase antibody, hybridization with a labeled probe with specific sequence from a known gene sequence for creatine amidinohydrolase, or polymerase chain reaction (PCR) using primers with said specific sequence, whereby DNA or CDNA containing the creatine amidinohydrolase gene can be selected or selectively amplified. If necessary, said gene can be incorporated into a vector to be transformed into a bacterial host, which is then incubated thereby propagating the gene of interest. Furthermore, if required, a restriction map of the obtained gene is made, and this gene is cleaved to give a fragment containing the creatine amidinohydrolase gene utilizing the restriction map. Thus, incorporating the obtained gene into a suitable vector (preferably plasmid), and applying mutagenesis thereto as mentioned below enables the DNA encoding the thermostable creatine amidinohydrolase of interest to be obtained.

Alternatively, if a known transformant containing a creatine amidinohydrolase gene is available, a vector (particularly a plasmid) containing the gene of interest can be collected therefrom according to usual methods. For example, the plasmid containing the gene of interest can be extracted and purified from *E.coli* JM109 (pUCE 100) (which has been deposited under the Budapest Treaty with National Institute of Bioscience and Human-Technology, Agency of Industrial Science and Technology (1-1-3, Higashi, Tsukuba, Ibaragi, Japan) under Accession Number: FERM BP-4803) which retains a recombinant plasmid pUCE 100 DNA (JP-A-8-89255 (1996)) containing a creatine amidinohydrolase gene from Alkaligenes sp. KS-85 strain which encodes an amino acid sequence of SEQ ID NO:1 by using QIAGEN (Funakoshi, Japan) or the like. DNA encoding the thermostable creatine amidinohydrolase of interest can be obtained by mutagenesis as mentioned below of the obtained plasmid.

Vector DNA usable in the invention includes a bacteriophage vector DNA, a plasmid vector DNA, etc. To be specific, vectors such as pUC118 (Takara Shuzo, Japan) and pBluescript (Stratagene, U.S.A.) are preferred.

A method for obtaining a thermostable creatine amidinohydrolase gene by a mutagenesis treatment of the recombinant plasmid containing DNA which encodes the creatine amidinohydrolase as obtained in the above procedures includes, but is not limited to, point mutation where the recombinant plasmid DNA is mutated at random with a chemical mutagen such as hydroxylamine or nitrous acid or by PCR, and site-specific mutagenesis, the technique being known to cause site-specific mutations comprising substitutions or deletions using a commercially available kit; a method where the above-mentioned recombinant plasmid DNA is selectively cleaved and the cleaved DNA is connected after deletion or addition of a selected oligonucleotide; and an oligonucleotide mutagenesis method. As for a mutagenesis method by genetic engineering, reference can be made to J. Sambrook et al., Molecular Cloning A Laboratory Manual (Second ed.), Cold Spring Harbor Laboratory Press, 1989, for example. Thus, the plasmid which contains DNA encoding a protein consisting of an amino acid sequence comprising mutations (i.e. deletions, substitutions, insertions, or additions of one or more amino acid residues) relative to an amino acid sequence of e.g. SEQ ID NO:1, and having thermostable creatine amidinohydrolase activity, can be obtained.

The recombinant DNA treated as above can be purified using a desalting column, QIAGEN (Funakoshi, Japan) or the like to obtain various recombinant DNAs.

Using thus obtained DNAs, *E.coli* K12, preferably *E.coli* JM 109 (TOYOBO, Japan), or XL1-Blue (Funakoshi, Japan) or the like can be transformed or transduced to obtain transformed or transduced microorganisms which contain recombinant DNAs carrying different creatin amidinohydrolase gene fragments.

In the case of the transformed microorganisms, for example, the following method can be adopted to obtain a strain which produces the thermostable creatine amidinohydrolase having desired properties (being thermostable and showing a decreased Km value) from the obtained transformants (in which the recombinant plasmid DNAs comprising different thermostable creatine amidinohydrolase genes are contained).

At first, each colony of the above obtained transformants is incubated in a liquid TY mecium (with addition of 50 $\mu$g Ampicilin and 1 mM IPTG) to inductively produce various kinds of thermostable creatine amidinohydrolase encoded in the recombinant plasmid DNAs. After incubation, the obtained culture is subjected to ultrasonic disintegration and extraction to heat-treat the crude enzyme extract for 30 min at 50° C., followed by measurement of the remaining activity and the Km value by Lineweaver-Burk plot. Furthermore, the measured results of each mutant are compared to those of a wild type protein which has been extracted, treated, and measured in the same manner, thereby selecting the transformant of interest.

To produce a thermostable creatine amidinohydrolase using the above obtained transformed or transduced microorganisms capable of producing the thermostable creatine amidinohydrolase, preferably using a strain belonging to the genus Escherichia, the following method can be employed.

The above microorganism may be incubated by a common solid culture method, but the application of a liquid culture method is preferred.

A medium usable for incubating the above microorganism comprises at least one nitrogen source such as yeast extract, peptone, meat extract, corn steep liquor, the effusion of soy bean or wheat koji, etc., with addition of at least one inorganic salt such as potassium dihydrogen phosphate, dipotassium hydrogen phosphate, magnesium sulfate, ferric chloride, ferric sulfate or manganese sulfate, and optionally, saccharide materials, vitamins, etc.

Adjustment of the initial pH of the medium to 7–9 is appropriate. Incubation is preferably performed at 30° C.–42° C., preferably around 37° C. for 6–24 hours by submerged aeration-agitation culture, shake culture, static culture, etc. After incubation, usual methods for collecting enzymes can be used to recover the thermostable creatine amidinohydrolase from the culture.

Cells are separated from the culture by subjecting it to such as filtration, centrifugation, etc., and then washed. The thermostable creatine amidinohydrolase is preferably collected from the cells. In such a case, the cells may be used as it is, however, it is preferred to collect the creatine amidinohydrolase therefrom by the following method; a method wherein cells are disintegrated with various disintegrators such as ultrasonic disintegrator, French press, dynamill, etc.; a method wherein the cell wall of the cells is lysed with such an enzyme as lysozyme and; or a method wherein an enzyme is extracted from the cells with a surfactant such as TritonX-100.

To isolate the thermostable creatine amidinohydrolase from the thus-obtained crude enzyme solution, usual methods for purifying an enzyme can be used. For example, a suitable combination of ammonium sulfate salting-out, organic solvent precipitation, ion-change chromatography, gel filtration chromatography, adsorption chromatography, electrophoresis, etc. is preferred.

The physicochemical properties of the obtained thermostable creatine amidinohydrolase are as follows.

Figure 2:
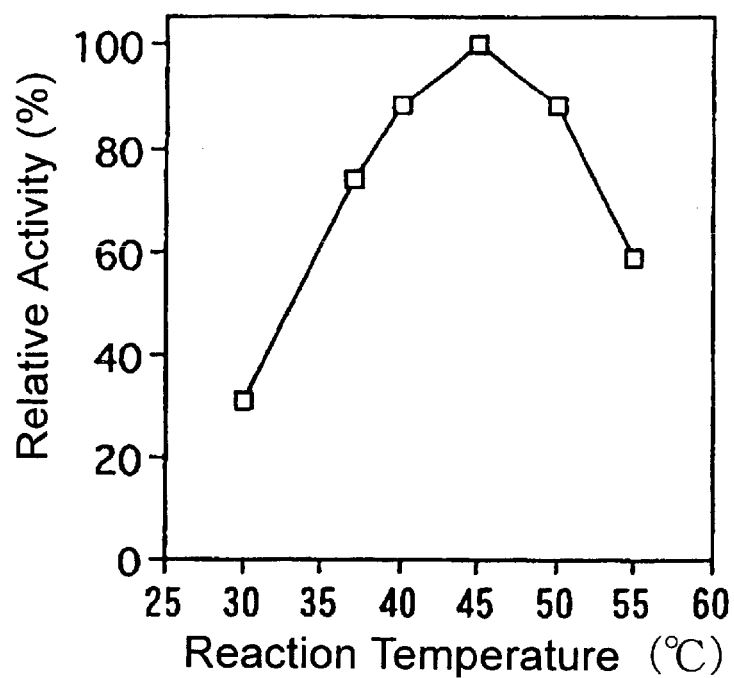
FIG. 2 shows the optimum temperature range of the enzyme of the invention.
Figure 3:
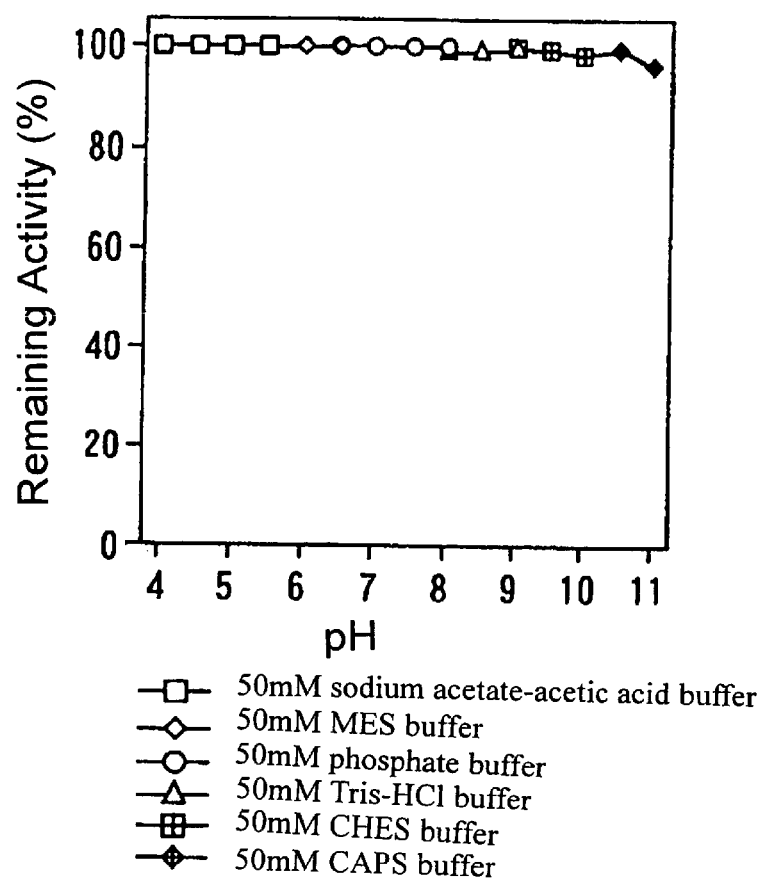
FIG. 3 shows the stable pH range of the enzyme of the invention.
Figure 4:
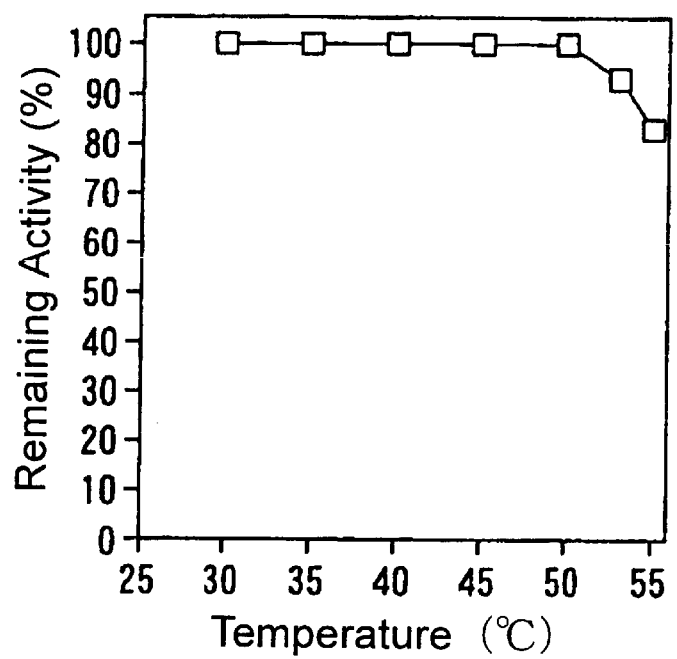
FIG. 4 shows the thermostability of the enzyme of the invention.

(1) Action: The enzyme hydrolyzes 1 mol of creatine to give 1 mol of sarcosine and 1 mol of urea;

(2) Substrate specificity: The enzyme has a substrate specificity to creatine;
(3) Optimum pH: The enzyme reaction at 37° C. for 10 min at each pH using the following buffers: 50 mM sodium acetate-acetic acid buffer (pH 4.0–5.5), 50 mM MES buffer (pH5.5–6.5), 50 mM phosphate buffer (pH 6.5–8.0), 50 mM Tris-HCl buffer (pH 8.0–9.0), 50 mM CHES buffer (pH 9.0–10.0), and 50 mM CAPS buffer (pH 10.0–11.0), indicates the relative activity shown in FIG. 1. As seen therefrom, the optimum pH of the enzyme is 7.0–8.0.
(4) Optimum temperature: Enzyme activity measured at different temperatures using a reaction solution with the same composition as the one used in the below-mentioned assay is shown in FIG. 2. As seen therefrom, the optimum temperature is around 45° C.
(5) Stable pH range: Remaining activity of the enzyme determined after treatment at 25° C. for 17 hours at pH 4.0–11.0 using the following buffer solutions: 50 mM sodium acetate-acetic acid buffer (pH 4.0–5.5), 50 mM MES buffer (pH5.5–6.5), 50 mM phosphate buffer (pH 6.5–8.0), 50 mM Tris-HCl buffer (pH 8.0–9.0), 50 mM CHES buffer (pH 9.0–10.0), and 50 mM CAPS buffer (pH 10.0–11.0), is shown in FIG. 3. As seen therefrom, the stable pH range is pH4.0–11.0.
(6) Thermostability: Thermostability measured after treatment at each temperature for 30 min using 50 mM Tris-HCl buffer (pH 7.5) is shown in FIG. 4. The enzyme of the invention is stable up to approximately 53° C.
(7) Assay for measuring enzyme activity: Enzyme activity is measured in the following conditions. One unit used herein indicates the enzyme activity which generates 1 $\mu$mol of urine per minute.
(Preparation of Reagents)
The First Solution: Substrate Solution
6.63 g of creatine is dissolved in 500 ml of 50 mM phosphate buffer (pH7.7).
The Second Solution: Color-development Solution
10 g of p-dimethylaminobenzaldehyde is dissolved in 500 ml of special grade ethanol, which is mixed with the mixture of 575 ml of resin-treated water and 75 ml of conc. hydrochloric acid.
(Measuring Procedure)
1) Preincubation of 0.9 ml of the first solution at 37° C. for 5 min.
2) Mixing 0.1 ml of an enzyme solution (adjusted to approximately 1–2 U/ml) thereto to allow reaction at 37° C. for 10 min
3) Mixing 2 ml of the above second solution
4) Allowing to stand the mixture at 25° C. for 20 min, followed by measurement of the absorbance at 435 nm (OD sample)
5) Blank value was measured by: incubating 0.9 ml of the first solution at 37° C. for 10 min; mixing 2 ml of the above second solution thereto; further mixing 0.1 ml of the enzyme solution thereto; allowing to stand the mixture at 25° C. for 20 min; and measuring the absorbance at 435 nm (ODblank)
(Calculation of Activity)
U/ml=$\Delta$OD×18.06×dilution rate
Herein, $\Delta$OD=ODsample-ODblank, and 18.06 is a coefficient calculated from a calibration curve of urine.
(8) Km value: The Km value of the enzyme measured with the above-mentioned assay method was 8.6 mM (for creatine) as determined from Lineweaver-Burk plot.
(9) Molecular weight: 92,000 Da (determined by gel filtration method).

EXAMPLES

Embodiments of the invention will be described below by means of illustration, but it is not intended that the scope of the invention is limited to these.

Example 1

(1) Preparation of a Recombinant Plasmid pUCE100DNA
E.coli JM109(pUCE100)(FERM BP-4803) was inoculated in 20 ml of TY medium (1% bacto-tryptone, 0.5% peptone, 0.25% NaCl), which was incubated at 37° C. for 18 hours while shaking, thereby obtaining the culture. The culture was then subjected to centrifugation at 6000 rpm for 10 min to harvest cells. A recombinant plasmid pUCE100 DNA was extracted therefrom and purified with QIAGEN tip-100 to obtain 70 $\mu$g of the DNA.
(2) Mutagenesis
XL1-RED (STRATAGENE) (upon proliferation, errors in plasmid replication occur readily, resulting in mutagenesis) is transformed with 2 $\mu$g out of 100 $\mu$g of the above recombinant plasmid DNA according to the method of D. M. Morrison (Method in Enzymology, 68, 326–331, 1979) to obtain approximately 1500 transformants. Among them, 500 colonies were all inoculated in 20 ml of the TY medium and incubated at 37° C. for 18 hours while shaking. After incubation, the culture was subjected to centrifugation at 6000 rpm for 10 min, to harvest cells. The plasmid pUCE100 was extracted therefrom and purified with QIAGEN tip-100 (Funakoshi, Japan) to obtain 70 $\mu$g of a mutated recombinant plasmid pUCE100DNA. E.coli JM109 strain (TOYOBO, Japan) was transformed using 5 $\mu$g of this plasmid to obtain approximately 2000 transformants retaining the mutated plasmid.
(3) Screening of a Mutant Having the Improved Thermostability and Reactivity to a Substrate
At first, each colony of the transformants obtained in the above is incubated in 2 ml TY medium (with addition of 50 $\mu$g Ampicilin and 1 mM IPTG), thereby allowing the induction of the various thermostable creatine amidinohydrolase genes contained in the plasmid. After incubation, the obtained culture was subjected to ultrasonic disintegration and extraction, and the crude enzyme extract was heat-treated at 50° C. for 30 min to determine the remaining activity; and the Km value was measured by Lineweaver-Burk plot with regard to the enzymes with good thermostability. Further, the measured result of each mutant was compared with that of a wild type creatine amidinohydrolase which was extracted and measured in the same manner to select a mutant being adequate for the purpose, thus the thermostable creatine amidinohydrolase was obtained form a mutant, E.coli JM109 (pUCE100 B-40).
E.coli JM109(pUCE100 B-40) has been deposited under the Budapest Treaty with National Institute of Bioscience and Human-Technology, Agency of Industrial Science and Technology (1-1-3, Higashi, Tsukuba, Ibaragi, Japan) under the accession number of FERM BP-6867. (This microorganism deposit was transferred as an international deposit on Sep. 2, 1999, from the national deposit FERM P-15971 deposited on Nov. 28, 1996.)

Example 2

Collection of the Thermostable Creatine Amidinohydrolase Enzyme
The mutant, E.coli JM109 (pUCE100B-40) obtained in Example 1 was incubated for 16 hours while shaking in a Sakaguchi flask containing 100 ml of TY medium (1% bacto-tryptone, 0.5% bacto-yeast extract, 0.5% NaCl, pH7.5) supplemented with 1 mM of isopropyl-$\beta$-D- galactoside, which was then flame-seeded in a 30 L fermenter containing 20 L of TY medium being prepared in the same manner. After seeding, it was incubated at 37° C. at 450 rpm for 20 hours under aeration of 20 L/min.

After incubation, the cells were harvested from 20 L of the culture mixture using Microza (Asahi Chemical Industry, Japan, PW-303), and washed with 20 mM phosphate buffer (pH7.5), then suspended in 10 L of the same buffer.

Step 1 (Preparation of the Crude Enzyme Solution)

20 g of lysozyme (in 50 mM phosphate buffer, pH7.5, 100 ml) and 1 L of 0.55M EDTA, pH8.0 were added to the above cell suspension (10 L) and mixed, which was allowed to stand at 30° C. overnight, then treated to remove nucleic acids by adding dropwise 500 ml of 5% protamine solution in water (pH8.0) with stirring. This solution was dialyzed against 10 mM CAPS-NaOH buffer (pH10.0) (referred to as buffer A hereinafter).

Step 2 (DEAE-cellulose Treatment)

Approximately 3 kg (by wet weight) of cellulose was added to the dialysate solution (approximately 28 L) and mixed, thereby adsorbing the thermostable creatine amidinohydrollase thereto, then the DEAE-cellulose was washed in buffer A containing 5% glycerine and 0.05%2-mercaptoethanol; and the thermostable creatine amidinohydrolase was eluted with buffer A containing 0.5M KCl, followed by ultrafiltration.

Step 3 (DEAE-Sepharose CL-4B (Pharmacia) Treatment)

Approximately 1.0 kg (by wet weight) of DEAE-Sepharose CL-4B which was buffered in buffer A was added to the condensate (approximately 1.0 L) from step 2 and mixed, thereby adsorbing the thermostable creatine amidinohydrolase thereto; then the DEAE-Sepharose CL-4B was washed in buffer A containing 0.05M KCl; and the thermostable creatine amidinohydrolase was eluted with buffer A, followed by ultrafiltration.

Step 4 (Sephacryl S-200 (Pharmacia) Treatment

The condensate (approximately 1.0 L) was molecular-sieved on Sephacryl S-200 filled in a column to collect 2.2 g of the active fraction. The specific activity of the fraction was 9U/OD280 nm. The properties of the obtained enzyme were the same as those mentioned in the above.

The present invention elucidated that the thermostable creatine amidinohydrolase can be produced efficiently.

While the invention can be carried out by those skilled in the art with various modifications or variations within the scope of the invention described in the attached claims or equivalents thereof, such modifications or variations are also intended to be included in the present invention.

All publications and patent applications cited herein are incorporated herein by reference in their entirety.

What is claimed is:

1. An isolated thermostable creatine amidinohydrolase that is isolated from *E. coli* JM109 (pUCE100B-40) (accession number FERM BP-6867), and which has the following physicochemical properties:

(a) hydrolyzing 1 mol of creatine to give 1 mol of sarcosine and 1 mol of urea;
(b) having a substrate specificity to creatine;
(c) having an optimum pH of 7.0 to 8.0;
(d) having a stable pH range of 4.0 to 11.0;
(e) having the optimum temperature of around 45° C.;
(f) being thermostable at 53° C.;
(g) having a molecular weight of 92,000 Da (as determined by gel filtration).

2. A process for producing the thermostable creatine amidinohydrolase of claim 1 comprising: incubating a culture of *E. Coli* JM 109 (pUCE100B-40) (accession number FERM BP-6867); and recovering said thermostable creatine amidinohydrolase from the culture.

* * * * *

UNITED STATES PATENT AND TRADEMARK OFFICE
CERTIFICATE OF CORRECTION

PATENT NO. : 6,821,766 B1
APPLICATION NO. : 09/869280
DATED : November 23, 2004
INVENTOR(S) : Keisuke Furukawa, Yasuji Koyama and Masaru Suzuki It is certified that error appears in the above-identified patent and that said Letters Patent is hereby corrected as shown below:

In the Sequence Listing, Sequence 1, position 79, "Pro" should read --Thr--.

In the Sequence Listing, Sequence 1, position 113, "Ala" should read --Arg--.

In the Sequence Listing, Sequence 1, position 140, "Asn" should read --Ala--.

In the Sequence Listing, Sequence 1, position 194, "Asp" should read --Glu--.

In the Sequence Listing, Sequence 1, position 195, "Met" should read --Val--.

In the Sequence Listing, Sequence 1, position 260, "Asn" should read --Thr--.

In the Sequence Listing, Sequence 1, position 261, "Pro" should read --Ala--.

In the Sequence Listing, Sequence 1, position 375, "Pro" should read --Arg--.

Signed and Sealed this

Twenty-second Day of July, 2008

JON W. DUDAS
*Director of the United States Patent and Trademark Office*